US00PP18400P3

(12) United States Plant Patent

Zaiger et al.

(10) Patent No.: US PP18,400 P3

(45) Date of Patent: Jan. 8, 2008

(54) NECTARINE TREE NAMED: 'HONEY LITE'

(50) Latin Name: *Prunus persica var. nucipersica*
Varietal Denomination: Honey Lite

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 101 days.

(21) Appl. No.: 11/320,293

(22) Filed: Dec. 29, 2005

(65) Prior Publication Data

US 2007/0157351 P1 Jul. 5, 2007

(51) Int. Cl.
*A01H 5/00* (2006.01)

(52) U.S. Cl. ..... Plt./190

(58) Field of Classification Search ..... Plt./190, Plt./187

See application file for complete search history.

*Primary Examiner*—Kent Bell
*Assistant Examiner*—Annette H Para

(57) ABSTRACT

A new and distinct variety of nectarine tree (*Prunus perscia* var. *nucipersica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. The tree having a winter chilling requirement of approximately 350 to 400 hours at or below 45° F.
2. A regular and productive bearer of large, clingstone fruit.
3. Fruit holding firm on the tree 7 to 8 days after maturity (shipping ripe).
4. Fruit with a high degree of attractive red skin color.
5. Vigorous, upright growth of tree.
6. Fruit with a mild, sweet, sub-acid flavor.

1 Drawing Sheet

Botanical classification: *Prunus persica* var. *nucipersica.*

BACKGROUND OF THE VARIETY

FIELD OF THE INVENTION

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine and peach trees, which are known to us, and mentioned herein, 'Royal Glo' Nectarine (U.S. Plant Pat. No. 8,281), 'Fairlane' Nectarine (non-patented), 'May Crest' Peach (U.S. Plant Pat. No. 4,064), 'May Grand' Nectarine (U.S. Plant Pat. No. 2,794), 'Earliglo' Nectarine (U.S. Plant Pat. No. 7,402), 'Honey Fire' Nectarine (U.S. Plant Pat. No. 12,418), 'Royal Gold' Peach (U.S. Plant Pat. No. 2,663) and 'Golden Supreme' Peach (non-patented).

ORIGIN OF THE VARIETY

The new and distinct variety of nectarine tree (*Prunus persica* var. *nucipersica*) was developed by us in our experimental orchard located near Modesto, Calif. as a first generation cross between two proprietary selected seedlings we developed with field identification numbers '59Z418' and '61Z355'. The maternal parent (59Z418) originated from crosses between the following varieties; 'Royal Glo' Nectarine (U.S. Plant Pat. No. 8,281), 'May Crest' Peach (U.S. Plant Pat. No. 4,064), 'May Grand' Nectarine (U.S. Plant Pat. No. 2,794), 'Earliglo' Nectarine (U.S. Plant Pat. No. 7,402), 'Fairlane' Nectarine (non-patented) 'Royal Gold' Peach (U.S. Plant Pat. No. 2,663) and 'Golden Supreme' Peach (non-patented). The paternal parent (61Z355) originated as an open pollinated seedling from seed of 'Honey Fire' Nectarine (U.S. Plant Pat. No. 12,418). A large number of these first generation seedlings were grown and budded to older trees of 'Nemaguard' Rootstock (non-patented), to excellerate rapid fruit production for evaluation. Under close and careful observation we recognized the desirable fruit characteristics of the present new variety and selected it for further asexual propagation and commercialization.

ASEXUAL REPRODUCTION OF THE VARIETY

Asexual reproduction of the new and distinct variety of nectarine tree was by buding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of nectarine tree (*Prunus perscia* var. *Nucipersica*) is of large size, vigorous, upright growth, a productive and regular bearer of large size, firm, yellow flesh, clingstone fruit with a mild, sweet, sub-acid flavor and excellent eating quality. The fruit is further characterized by having good storage, handling, with shipping quality and holding firm on the tree 7–8 days after maturity (shipping ripe), having an attractive red skin color and being relatively uniform in size and maturity throughout the tree. In comparison to the proprietary maternal parent '59Z418' the new variety has larger size fruit with sub-acid flesh compared to acid, has a higher degree of attractive red skin and the tree is approximately 100 hours lower in its winter chilling requirement. In comparison to its proprietary pollen parent '61Z355', the new variety has larger fruit with more attractive red skin color and the fruit is more uniform in size throughout the tree, both varieties have sweet, sub-acid flesh.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of nectarine tree, 5 years of age, its flowers, foliage and fruit, as based on observations of 5 year old specimens grown near Modesto, Calif., with color in accordance with Munsell Book of Color.

Tree:

*Size.*—Large, normal for the majority of most commercial varieties of nectarine trees. Pruned to 3 to 3.5 meters in height for economical harvesting of fruit. Average spread 3 meters, varies with different cultural practices.

*Vigor.*—Vigorous, tree growth of 1.5 to 2 meters the first growing season. Varies slightly with fertility, type of soil and cultural practices.

*Form.*—Upright, usually pruned to vase shape.

*Branching habit.*—Upright, crotch angle approximately 30°, increases with heavy crop load.

*Productivity.*—Productive, normal thinning and spacing of fruit desirable. Fruit set varies with climatic conditions at bloom time.

*Bearer.*—Regular, adequate fruit set 3 consecutive years, no alternate bearing observed.

*Fertility.*—Self fertile.

*Density.*—Medium dense, pruning to vase shape opens centers to more sunlight to enhance fruit color and health of fruit wood.

*Hardiness.*—Hardy in all stone fruit areas of California. Tree grown in USDA Hardiness Zone 9. Winter chilling requirement approximately 350 to 400 hours at or below 45° F.

Trunk:

*Size.*—Large. Average circumference 58.4 cm at 22.8 cm above ground on a 5 year old tree.

*Stocky.*—Medium.

*Texture.*—Medium shaggy, roughness increases with age.

*Color.*—Varies from 10YR 3/6 to 2.5Y 7/2.

Branches:

*Size.*—Medium. Average circumference 18.6 cm at 1.2 meters above ground. Crotch angle approximately 30°.

*Surface texture.*—New growth relatively smooth. Mature growth varies from medium to rough, roughness increases with age.

*Lenticels.*—Average number 15 in a 25.8 square cm section. Average length 2.5 mm. Average width 1.1 mm. Color varies from 7.5YR 6/8 to 10YR 6/10.

*Color.*—New growth varies from 2.5GY 5/4 to 2.5GY 4/4. Mature growth varies from 10YR 3/4 to 2.5Y 3/4, varies with age of growth.

Leaves:

*Size.*—Large. Average length 125.8 mm. Average width 38.2 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slight indentations over midrib and leaf veins, glabrous. Lower surface relatively smooth, small ridges created by midrib and pinnate venation, glabrous.

*Petiole.*—Size — medium. Average length 11.4 mm. Average width 1.6 mm. Longitudinally grooved. Surface — glabrous. Color varies from 2.5GY 5/8 to 5GY 5/6.

*Glands.*—Reniform. Medium. Average length 1.3 mm. Average diameter 0.7 mm. Number varies from 3 to 5, average number 4. Located primarily on base of leaf blade and upper portion of petiole. Color varies from 5GY 6/6 to 5GY 5/6.

*Color.*—Upper surface varies from 5GY 3/6 to 7.5GY 3/4. Lower surface varies from 5GY 4/4 to 7.5 GY 4/4. Midvein color varies from 2.5GY 7/6 to 5GY 7/6.

Flower buds:

*Size.*—Large. Average length 17.1 mm. Average diameter 11.3 mm.

*Hardiness.*—Hardy in all stone fruit growing areas of California, with respect to California winters. Grown in USDA Hardiness Zone 9.

*Form.*—Conical, becoming elongated before opening.

*Pedicel.*—Average length 3.5 mm. Average width 1.4 mm. Color varies from 2.5GY 5/8 to 5GY 6/6.

*Color.*—Varies from 7.5RP 6/12 to 5RP 7/8.

Flowers:

*Size.*—Large, showy. Average height 17.8 mm. Average diameter 45.3 mm.

*Petals.*—Number — 5, alternately arranged to sepals. Large. Average length 21.1 mm. Average width 19.5 mm. Shape varies from elliptic to orbicular. Margin — sinuate, slightly cupped. Both surfaces glabrous.

*Sepals.*—Number — 5, alternately arranged to petals. Size — large. Average length 4.7 mm. Average width 4.2 mm. Shape — ovate, apex rounded. Margin — entire. Surface — upper surface glabrous, lower surface pubescent. Color — upper surface varies from 2.5GY 5/8 to 5GY 5/6. Lower surface varies from 7.5R 2/4 to 10R 2.6.

*Stamens.*—Average number per flower 42. Average filament length 13.1 mm. Filament color varies from 7.5RP 9/2 to N 9.5/ (white). Anther color varies from 5R 4/10 to 5R 3/10.

*Pollen.*—Self fertile. Color varies from 5Y 8/10 to 5Y 7/12.

*Pistil.*—Normally 1, varies from 1 to 2. Surface — glabrous. Average length 15.5 mm. Position of stigma — even in height with anthers. Color varies from 2.5GY 8/8 to 5GY 7/10.

*Fragrance.*—Moderate.

*Blooming period.*—Date of First Bloom Feb. 17, 2005. Date of Petal Fall Feb. 27, 2005, varies slightly with climatic conditions.

*Number of flowers per flower bud.*—One.

*Color.*—Varies from 5RP 8/6 to 7.5RP 9/2, fades with age.

*Pedicel.*—Average length 3.6 mm. Average width 1.5 mm. Color varies from 2.5GY 6/6 to 5GY 7/8.

Fruit:

*Maturity when described.*—Firm ripe.

*Date of first picking.*—May 31, 2005.

*Date of last picking.*—Jun. 8, 2005, varies slightly with climatic conditions.

*Size.*—Large. Average diameter axially 66.5 mm. Average transversely in suture plane 66.5 mm. Average weight 178.9 grams, varies slightly with fertility of the soil, amount of thinning and climatic conditions.

*Form.*—Globose.

*Suture.*—Lipped, extends from base to apex.

*Ventral surface.*—Lipped, extent varies slightly between fruit.

*Apex.*—Slightly retuse.

*Base.*—Varies from flat to slightly retuse.

*Cavity.*—Rounded to slightly elongated in suture plane. Average depth 5.5 mm. Average diameter 14.1 mm.

Stem:

*Size.*—Small to medium. Average length 7.4 mm. Average diameter 4.6 mm.

*Color.*—Varies from 2.5GY 5/6 to 2.5GY 5/8.

Flesh:

*Ripens.*—Evenly.

*Texture.*—Firm, meaty.

*Fibers.*—Few, small, tender.

*Firmness.*—Firm, holds firm on the tree 7 to 8 days after maturity (shipping ripe).

*Aroma.*—Slight.

*Amydgalin.*—Undetected.

*Eating quality.*—Excellent.

*Flavor.*—Excellent, mild, sweet, sub-acid flavor.

*Juice.*—Moderate, enhances flavor.

*Brix.*—Average Brix 11.7°, varies slightly with amount of fruit per tree and climatic conditions.

*Color.*—Varies from 2.5Y 8.5/12 to 2.5 Y 8/10. Pit cavity varies from 2.5Y 7/8 to 2.5Y 7/10.

Skin:

*Thickness.*—Medium.

*Surface.*—Smooth.

*Down.*—Wanting.

*Tendency to crack.*—Very slight.

*Color.*—Ground color varies from 5Y 8.5/8 to 5Y 8/8. Overspread with 5R 2/6 to 7.5R 3/10 on approximately 90% of fruit surface.

*Tenacity.*—Tenacious to flesh.

*Astringency.*—None.

Stone:

*Type.*—Clingstone.

*Size.*—Large. Average length 39.5 mm. Average width 30.0 mm. Average depth 23.6 mm.

*Form.*—Obovoid.

*Base.*—Varies from flat to rounded.

*Apex.*—Pointed. Average length 1.9 mm.

*Surface.*—Pitted throughout, pits vary from rounded to elongated. One furrow on each side of suture.

*Sides.*—Unequal with one side extending slightly further from suture plane.

*Ridges.*—Relatively smooth, broad ridges extending from base toward apex.

*Tendency to split.*—None.

*Color.*—Varies from 10YR 7/6 to 10YR 6/8 when dry.

Kernal:

*Form.*—Ovate.

*Viability.*—Poor viability, embryo incomplete.

*Size.*—Medium to large. Average length 18.9 mm. Average width 12.4 mm. Average depth 6.2 mm.

*Skin color.*—Varies from 5Y 9/6 to 5Y 8.5/6, when dry.

Use: Dessert. Market — local and long distance.

Keeping quality: Good, held firm in cold storage at 38° F. to 42° F. for 2 weeks without internal breakdown or appreciable loss of flavor.

Shipping quality: Good, minimal bruising of flesh or skin scarring during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of nectarine tree (*Prunus persica* var. *nucipersica*), substantially as illustrated and described, characterized by its large size, vigorous, upright growth, being a productive and regular bearer of large size, firm, yellow flesh, clingstone fruit with a mild, sweet, sub-acid flavor and excellent eating quality; the fruit is further characterized by having an attractive red skin color, holding firm on the tree 7 to 8 days after maturity (shipping ripe) and having good storage and shipping quality.

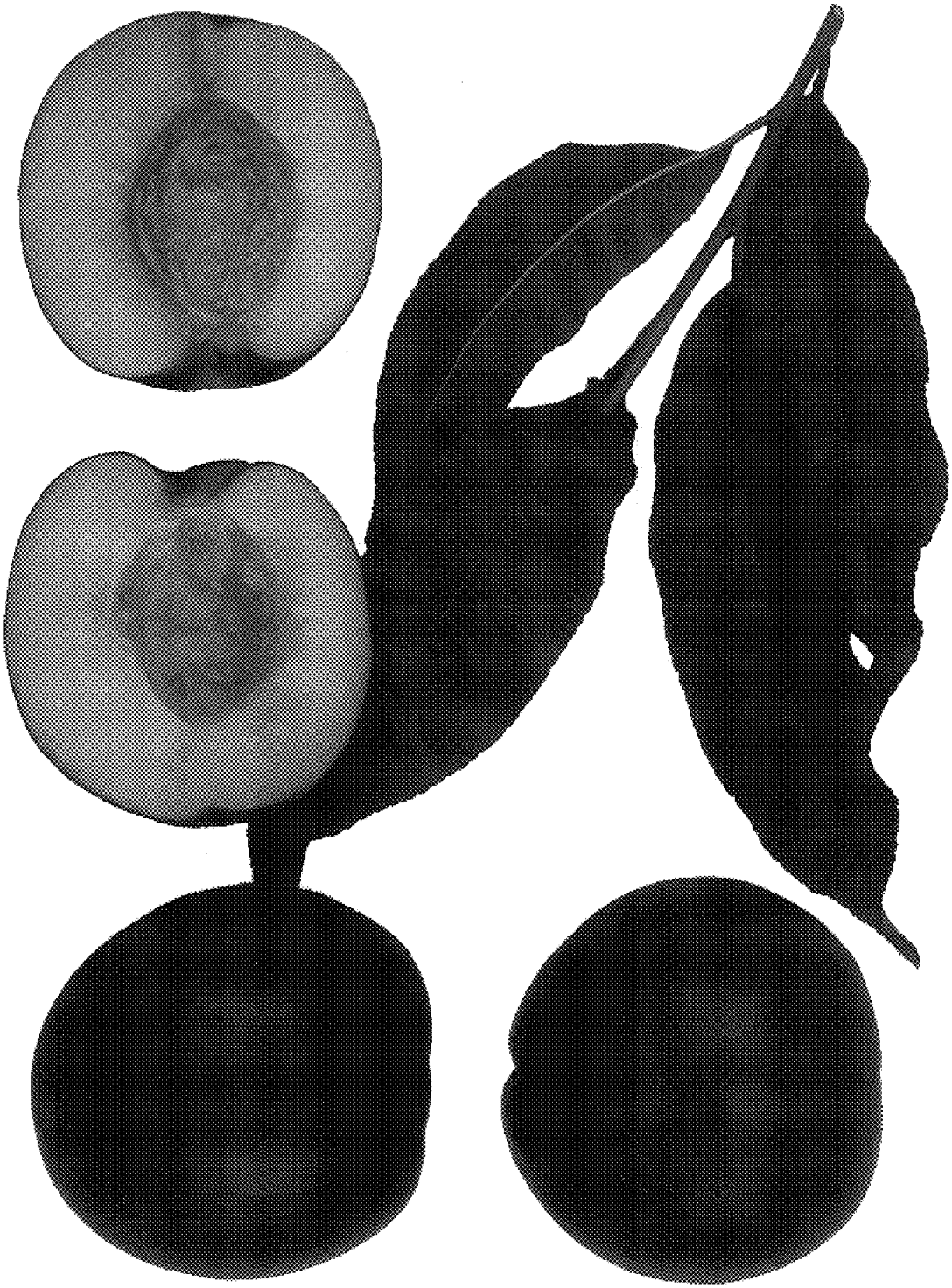

* * * * *